US010512664B2

(12) United States Patent
Lamb et al.

(10) Patent No.: US 10,512,664 B2
(45) Date of Patent: *Dec. 24, 2019

(54) ANTIVIRAL COMPOSITIONS AND METHODS (71) Applicant: RALCO NUTRITION, INC., Marshall, MN (US)

(72) Inventors: Richard Dale Lamb, Balaton, MN (US); Tom M. Lattimore, Good Thunder, MN (US)

(73) Assignee: Ralco Nutrition, Inc., Marshall, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/327,112

(22) PCT Filed: Jul. 22, 2015

(86) PCT No.: PCT/US2015/041592
§ 371 (c)(1),
(2) Date: Jan. 18, 2017

(87) PCT Pub. No.: WO2016/014699
PCT Pub. Date: Jan. 28, 2016

(65) Prior Publication Data
US 2017/0157190 A1   Jun. 8, 2017

Related U.S. Application Data

(60) Provisional application No. 62/027,592, filed on Jul. 22, 2014.

(51) Int. Cl.
| A61K 31/05 | (2006.01) |
| A61K 31/53 | (2006.01) |
| A61K 31/11 | (2006.01) |
| A61K 36/53 | (2006.01) |
| A01N 27/00 | (2006.01) |
| A01N 31/08 | (2006.01) |
| A01N 35/02 | (2006.01) |
| A01N 65/22 | (2009.01) |
| A01N 65/24 | (2009.01) |

(52) U.S. Cl.
CPC .............. *A61K 36/53* (2013.01); *A01N 27/00* (2013.01); *A01N 31/08* (2013.01); *A01N 35/02* (2013.01); *A01N 65/22* (2013.01); *A01N 65/24* (2013.01); *A61K 31/05* (2013.01); *A61K 31/11* (2013.01)

(58) Field of Classification Search
None
See application file for complete search history.

(56) References Cited

U.S. PATENT DOCUMENTS

| 247,940 | A | 10/1881 | Mix |
| 6,355,684 | B1 | 3/2002 | Squires |
| 6,399,356 | B1 | 6/2002 | Bernhardt et al. |
| 6,541,042 | B1* | 4/2003 | Frater-Schroder ............ A61K 31/045 424/725 |
| 6,680,074 | B1 | 1/2004 | Morice |
| 6,703,056 | B2* | 3/2004 | Mehansho ............ A23C 9/1542 426/573 |
| 7,048,953 | B2 | 5/2006 | Vail, III et al. |
| 8,158,687 | B2* | 4/2012 | Yaghmur ............... A23D 7/011 426/89 |
| 8,507,734 | B2 | 8/2013 | Chen et al. |
| 2005/0014827 | A1* | 1/2005 | Schur ................... A01N 65/00 514/553 |
| 2007/0036831 | A1* | 2/2007 | Baker ................. A61K 31/573 424/400 |
| 2007/0154504 | A1 | 7/2007 | Coats et al. |
| 2009/0004308 | A1 | 1/2009 | Frehner et al. |
| 2009/0186096 | A1 | 7/2009 | Kritzman et al. |
| 2011/0076306 | A1* | 3/2011 | Rodriguez ........... A61K 31/715 424/244.1 |
| 2011/0150995 | A1 | 6/2011 | Joshi |
| 2012/0093952 | A1 | 4/2012 | Frehner et al. |
| 2012/0219602 | A1 | 8/2012 | Flack et al. |
| 2013/0131121 | A1 | 5/2013 | Tsuchida et al. |
| 2013/0252909 | A1 | 9/2013 | Kraus et al. |

(Continued)

FOREIGN PATENT DOCUMENTS

| JP | 56015831 | 2/1981 |
| WO | 9842188 A1 | 10/1998 |
| WO | 2008155536 A1 | 12/2008 |

(Continued)

OTHER PUBLICATIONS

"Food Additive Code Numbers", downloaded Apr. 14, 2018 from https://millenniumeducation.com/food-additive-code-numbers/ (Year: 2018).*

Pietro Buzzini, Panagiotis Arapitsas, Marta Goretti, Eva Branda, Benedetta Turchetti, Patrizia Pinelli, F. Ieri, and Annalisa Romani. Antimicrobial and Antiviral Activity of Hydrolysable Tannins. Mini-Reviews in Medicinal Chemistry, 2008, 8, 1179-1187. (Year: 2008).*

Jürgen Reichling, Paul Schnitzler, Ulrike Suschke, and Reinhard Sailer. Essential Oils of Aromatic Plants with Antibacterial, Antifungal, Antiviral, and Cytotoxic Properties—an Overview. Forsch Komplementmed 2009;16:79-90. (Year: 2009).*

(Continued)

*Primary Examiner* — Michael P Cohen
(74) *Attorney, Agent, or Firm* — Billion & Armitage; Benjamin C. Armitage (57) ABSTRACT

In general, embodiments of the present invention provide antiviral essential oil compositions, and methods of making and using the same. Essential oil compositions can include one or more essential oils, such as thyme essential oil, oregano essential oil, and/or cinnamon essential, optionally in combination with one or more emulsifiers. Essential oil compositions can be in the form of an emulsion and have droplet sizes less than about 25 microns. The use of these compositions in organisms and systems provides beneficial antiviral effects, among others.

15 Claims, 1 Drawing Sheet

(56) References Cited

U.S. PATENT DOCUMENTS

2014/0030203 A1  1/2014  Dombeck

FOREIGN PATENT DOCUMENTS

WO  WO 2012076717 A1 *  6/2012  ........... A61K 9/0019
WO  WO-2012076717 A1 *  6/2012  ........... A61K 9/0019

OTHER PUBLICATIONS

M.E. Osman, P.A. Williams, A.R. Menzies, and G.O. Phillips. Characterization of Commercial Samples of Gum Arabic. J. Agric. Food Chem. 1993, 41, 71-77. (Year: 1993).*

Akram Astani, Jürgen Reichling and Paul Schnitzler. Comparative Study on the Antiviral Activity of Selected Monoterpenes Derived from Essential Oils. Phytother. Res. 24: 673-679 (2010). (Year: 2010).*

LL Theisen, et al. Tannins from Hamamelis virginiana Bark Extract: Characterization and Improvement of the Antiviral Efficacy against Influenza A Virus and Human Papillomavirus. PLoS ONE 9(1): e88062. Published Jan. 31, 2014. (Year: 2014).*

Jürgen Reichling, Paul Schnitzler, Ulrike Suschke, Reinhard Saller. Essential Oils of Aromatic Plants with Antibacterial, Antifungal, Antiviral, and Cytotoxic Properties—an Overview. Forsch Komplementmed 2009;16:79-90. (Year: 2009).*

Engel Apotheke website entry for Caelo Thyme Oil (downloaded Sep. 12, 2018 from https://www.engel-apotheke-aachen.de/shop/Thymianoel-ProFuma-Caelo-HV-P (Year: 2018).*

D. Renard, C. Garnier, A. Lapp, C. Schmitt, C. Sanchez. Structure of arabinogalactan-protein from Acacia gum: From porous ellipsoids to supramolecular architectures (Carbohydrate Polymers 90 (2012) 322-332). (Year: 2012).*

J. Gutierrez, C. Barry-Ryan, P. Bourke. The antimicrobial efficacy of plant essential oil combinations and interactions with food ingredients. International Journal of Food Microbiology 124 (2008) 91-97 (Year: 2008).*

C. Koch, J. Reichling, J. Schneele, P. Schnitzler. Inhibitory effect of essential oils against herpes simplex virus type 2. Phytomedicine 15 (2008), pp. 71-78. (Year: 2008).*

Bassole, et al., "Essential oils in Combination and Their antimicrobial Properties", Molecules, vol. 17, 2012, 3989-4006.

Hyldgaard, et al., "Essential oils in food preservation: mode of action, synergies, and interactions with food matrix components", Frontiers in Microbiology, Jan. 2012, vol. 3, Article 12, Jan. 25, 2012, pp. 1-24.

PCT/US2015/041592, "International Search Report and Written Opinion", dated Oct. 29, 2015, 9 pages.

Havashi, et al., "Inhibitory effect of Cinnamaldehyde, derived from Cinnamomi cortex, on the growth of influenza A/PR/8 virus in vitro and in vivo", Antiviral Res., 74/1, Jan. 26, 2007, 1-8.

Liu, et al., "The antidenovirus activities of cinnamaldehyde in vitro", Laboratory Medicine, 40/11, Nov. 2, 2009, 669-674.

* cited by examiner

ANTIVIRAL COMPOSITIONS AND METHODS

CROSS-REFERENCE TO RELATED APPLICATION

This application claims benefit of U.S. Provisional Application No. 62/027,592, filed on 22 Jul. 2014 and which application is incorporated herein by reference. A claim of priority is made.

BACKGROUND

Viruses are the most abundant biological entities on Earth, and are classified by the Baltimore Scheme into seven genomic groups based on the chemical type, number of strands, and strand translation ability of each virus: I: dsDNA viruses, II: ssDNA viruses (+strand or "sense") DNA, III: dsRNA viruses, IV: (+)ssRNA viruses (+strand or sense) RNA, V: (−)ssRNA viruses (strand or antisense) RNA, VI: ssRNA-RT (reverse transcriptase) viruses (+strand or sense) RNA with DNA intermediate in life-cycle, and VII: dsDNA-RT (reverse transcriptase) viruses. Each group contains enveloped and non-enveloped viruses, which share similar behavioral and structural similarities.

Viruses infecting domesticated and wild animals pose substantial economic and sustainability threats to commercial operations and natural ecosystems. Many viruses can be spread without direct contact between infected animals and potential hosts, such as epizootic hemorrhagic disease (EHD) which is spread by biting midges, and accordingly can rampantly spread through captive populations and wild ecosystems regardless of host animal proximity. In an example, porcine reproductive and respiratory syndrome (PRRS) became pandemic in the 1990s and has caused an estimated annual economic loss of $600 million in the United States. In equine populations, equine herpesvirus-1 (EHV1) can cause spontaneous abortion of foals, respiratory infection, and neurological symptoms.

Viral infections of animals have been combatted with vaccines and pharmaceuticals, which require evaluation and approval from the USDA, FDA, and EPA. However, viral mutations can render many of these treatment methods ineffective. Further, inadequate resources and delayed regulatory approval can hinder vaccine and pharmaceutical development necessary to pace with viral mutations. Vaccines and pharmaceuticals can also persist in the environment almost indefinitely, and bioaccumulate to dangerous levels. Moreover, many antiviral treatments are inherently detrimental to host subjects, but are used due to the absence of alternatives. Human immunodeficiency treatments are an example, which are not capable of completely eliminating HIV from the host subject, yet leave the host subject body and immune system in a weakened state.

SUMMARY

In general, this disclosure describes techniques for antiviral compositions comprising essential oils. Techniques further describe methods for providing antiviral effects within an organism. Embodiments for methods for suppressing proliferation of a virus within an organism comprise administering an effective amount of an antiviral composition to a subject, wherein the antiviral agent comprises one or more essential oils and administration of the antiviral composition provides an antiviral effect within the organism.

In some embodiment, an antiviral treatment composition can comprise one or more essential oils and an emulsifier, wherein the emulsifier comprises a tannin compound, arabinogalactan and combinations thereof.

In other embodiments, an antiviral treatment composition can comprise synthetic cinnamaldehyde and one or more essential oils from the Lamiaceae family, and optionally an emulsifier.

In other embodiments, a method of inhibiting a virus within a subject or system can comprise administering a treatment composition to one or more of a subject or system, wherein the treatment composition comprises one or more essential oils and one or more of arabinogalactan or a tannin compound.

In other embodiments, a method of inhibiting a virus within a subject or system can comprise administering a treatment composition to one or more of a subject or system, wherein the treatment composition comprises one or more of thyme essential oil, oregano essential oil, or cinnamon essential oil, and an emulsifier, wherein the one or more essential oils are present as an emulsion and the average particle size of the one or more essential oils in the emulsion is less than about 25 microns.

The details of one or more examples are set forth in the accompanying drawings and the description below. Other features, objects, and advantages will be apparent from the description and drawings, and from the claims.

BRIEF DESCRIPTION OF THE DRAWINGS

The accompanying drawings illustrate non-limiting example embodiments of the invention.

DETAILED DESCRIPTION

The present invention provides antiviral essential oil (EO) compositions which are environmentally friendly, are resistant to viral mutation, and can be administered to subjects as a general health suite which provides health benefits beyond antiviral benefits. Further, EO compositions provided herein are effective against viruses in all seven Baltimore Scheme groups.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Definitions

As used herein, the recited terms have the following meanings. All other terms and phrases used in this specification have their ordinary meanings as one of skill in the art would understand after review of this disclosure.

As used herein, the terms "EOs" or "essential oils" refer to aromatic, volatile liquids extracted from organic material, such as plants. EOs are often concentrated hydrophobic liquids containing volatile aroma compounds. EO chemical constituents can fall within general classes, such as terpenes (e.g., p-Cymene, limonene, sabinene, a-pinene, y-terpinene, b-caryophyllene), terpenoids (e.g., citronellal, thymol, carvacrol, carvone, borneol), phenylpropanoids (e.g., cinnamaldehyde, eugenol, isoeugenol, vanillin, safrole), and other degradation products originating from unsaturated fatty acids, lacones, terpenes, glycosides, and sulfur and nitrogen-containing compounds (e.g., allicin, allyl isothiocyanate). Terpenes can include, for example, monoterpenes ($C_{10}H_{16}$), sesquiterpenes ($C_{15}H_{24}$), and other longer chains including diterpenes ($C_{20}H_{32}$), triterpenes ($C_{30}H_{40}$), etc. Terpanoids can include, for example, chemical or biochemical modifications of terpenes. EO chemical constituents can include functional groups such as ethers, phenols, ketones, alcohols, and oxides. EOs can be natural (i.e., derived from plants), or synthetic.

EOs can be derived from the flowers, fruits, seeds, leaves, stalks, barks, roots, and rhizomes of sources including, but not limited to, one or more of African basil, bishop's weed, cinnamon, clove, coriander, cumin, garlic, kaffir lime, lime, lemongrass, mustard oil, menthol, oregano, rosemary, savory, Spanish oregano, thyme, sage, mint, citrus fruit, geranium, aniseed, *eucalyptus*, camphor, calumus, cedarwood, citronella, nutmeg, vetiver, wintergreen, ylang-ylang, neroli, sandalwood, frankincense, ginger, peppermint, jasmine, spearmint, patchouli, rosewood, vanilla, bergamot, balsam, Hinoki, Hiba, ginko, pomegranate, manuka, calendula, palmarosa, jojoba, tea tree, coconut, lavender, and combinations thereof, for example. In many cases, "EO" refers to polychemical blends which include a number of different chemical species, such as 2 to 15 chemical species, or 2 to 50 chemical species. Some EO sources can contain a single primary species; for example, cinnamon oil can comprise about 85% to about 90% cinnamaldehyde. Some EOs can contain two primary species; for example, citronella oil can comprise about 35% to about 50% citronellal, and about 35% to about 45% geraniol.

As used herein, "plants" and "plant derivatives" can refer to any portion of a growing plant, including the roots, stems, stalks, leaves, branches, berries, seeds, flowers, fruits, bark, wood, rhizomes, resins, and the like. For example, cinnamon EO can be derived from the leaves or bark of a cinnamon plant.

As used herein "cinnamon EO" refers to one or more of natural cinnamon oil (i.e., EO derived from plants in the *Cinnamomum* genus), or synthetic cinnamon oil. Synthetic cinnamon EO can comprise synthetic cinnamaldehyde. Synthetic cinnamon EO can further comprise one or more major constituents of natural cinnamon EO. A major constituent is one which comprises at least 1 wt. %, at least 2.5 wt. %, or at least 5 wt. % of a natural EO assay.

As used herein "thyme EO" refers to one or more of natural thyme oil (i.e., EO derived from plants in the *Thymus* genus), or synthetic thyme oil. Synthetic thyme EO can comprise synthetic thymol. Synthetic thyme EO can further comprise one or more major constituents of natural thyme EO.

As used herein "oregano EO" refers to one or more of natural oregano oil (i.e., EO derived from plants in the *Origanum* genus), or synthetic oregano oil. Synthetic oregano EO can comprise synthetic carvacrol. Synthetic oregano EO can further comprise one or more major constituents of natural oregano EO.

As used herein, the term "agitate" refers to exerting an outside force on a material, such as stirring, shaking, or vibrating. A vessel can be agitated by turning, tipping, shaking, etc. A paddle or stirrer can be utilized within a vessel to agitate, for example.

As used herein, the term "emulsion" refers to a system containing two or more liquids, in which at least one liquid is not substantially soluble or miscible in at least one other liquid. In an emulsion, one liquid, the "dispersed phase", is dispersed throughout a second liquid, the "continuous phase", and is often present as a fine dispersion of droplets. An EO may be emulsified or substantially emulsified within a carrier medium, such as water. In this example, the water is the continuous phase, and the EO is the dispersed phase present as a dispersion of droplets. An emulsion can optionally include an emulsifier and/or stabilizer, which can encourage the formation of the droplets by the dispersed phase, maintain the size or shape of the dispersed phase droplets, assist in reducing or reduce the size of the dispersed phase droplets, or combinations thereof. Emulsions can significantly increase the surface area of a dispersed phase. Some emulsions can further comprise dispersed insoluble particles such as solid carriers, mineral chelates, mineral salts, or the like. A low droplet size of a dispersed phase can advantageously aid in the dispersion of insoluble particles throughout the continuous phase.

As used herein, the term "emulsifier" refers to a substance that stabilizes an emulsion. The emulsifier can utilize physical properties, chemical properties, or utilize both physical and chemical properties to interact with one or more substances of an emulsion. Tannic acid is an example of an emulsifier for EOs and water.

As used herein, the term "tannin compound" refers to a polyphenolic biomolecule including at least twelve hydroxyl groups and at least five phenyl groups Tannin compounds include compounds utilizing gallic acid, flavone and phloroglucinol as base units. Tannic acid ($C_{76}H_{52}O_{46}$) is one form of a tannin compound. Tannic acid can include quercitannic acid and gallotannic acid, for example.

As used herein, "carrier" refers to a substance that physically or chemically binds or combines with a target or active substance to facilitate the use, storage, or application of the target or active substance. Carriers are often inert materials, but can also include non-inert materials when compatible with the target or active substances. Examples of carriers include, but are not limited to, water for compositions that benefit from a liquid carrier, or diatomaceous earth or limestone for compositions that benefit from a solid carrier.

The disclosure herein indicates the efficacy of compositions comprising a plurality of EOs which provide a synergistic effect beyond EOs utilized in isolation. Further, EO compositions provided herein do not exhibit antagonistic effect between EO moieties within a composition. An EO composition generally includes an EO fraction and optionally one or more additional components. The ratio of the EC) fraction to the one or more additional components in a composition can depend on several factors such as administration method, and the nutritional/health needs and/or palate of a consuming subject, among others. In many embodiments, a consuming subject comprises an animal or a human. Compositions can comprise additional components including carriers, emulsifiers, and stabilizers, among others. Compositions can be in the form of an emulsion.

EO compositions provided herein are directly effective against viruses and viral infections. Viral infections can be latent, active, or reactivated. Antiviral efficacy can be measured by a percent reduction in viral concentration within a given system or host organism as caused by an EO composition. A host organism can include ruminant and non-ruminant animals. Antiviral EO compositions provided herein can effect up to about a 43% reduction in viral concentration, up to about a 68% reduction in viral concentration, up to about a 82% reduction in viral concentration, up to about a 98% reduction in viral concentration, up to about a 99% reduction in viral concentration, up to about a 99.99% reduction in viral concentration, or greater than about a 99.99% reduction in viral concentration within a given host organism or system. A system can include, for example, an animal blood bank or an animal feed storage tank. EO composition antiviral efficacy can also be characterized by preventing viral propagation within a host organism, or preventing viral propagation within a host organism beyond a threshold concentration or particular region of a host organism. A threshold concentration can include a minimum concentration required for a virus to infect cells, or a maximum concentration at which a virus cannot infect cells.

Embodiments of EO compositions provided herein are effective against enveloped viruses, non-enveloped viruses, or both. Viruses generally propagate within a host in an iterative fashion that includes binding to a host cell, injecting viral genome into the host cell, and replicating the viral genome within the host cell. Non-enveloped viruses contain proteins on the capsid which can identify and bind the virus to receptors on a host cell. EO compositions provided herein disable this "lock and key" mechanism, preventing a virus from infecting host cells. Enveloped viruses include a lipid membrane or envelope obtained from a previous host cell which isolate the viral body from a host immune system. Glycoproteins on the envelope surface allow a virus to identify and fuse to membranes of subsequent host cells, after which the viral capsid and genome enter and infect the host cell. EO compositions can impair, disable, or destroy viral envelopes, thereby preventing the virus from identifying host cells, fusing to host cells, or protecting the viral body against a host immune system. As a result of these non-limiting proposed antiviral mechanisms, the compositions provided herein are generally effective against most or all strains of a given virus, unlike many vaccine and pharmaceutical compositions which can be specific to only one viral strain. EO compositions provided herein can be administered in combination with vaccines and pharmaceuticals.

The EO compositions provided herein are effective against viruses in all seven Baltimore Classification genomic groups. In particular, the EO compositions provided herein are effective against the following non-limiting list of viruses: viruses from the genus *Pestivirus* (e.g., bovine viral diarrhea virus, Baltimore group IV), viruses from the genus *Varicellovirus* (e.g., equine herpesvirus-1, Baltimore group I), parvovirus (Baltimore group II), viruses from the enterovirus genus (e.g., enterovirus 71, also known as "hand foot and mouth disease", Baltimore group IV), MS-2 bacteriophage virus, viruses from the Reoviridae family (e.g., bovine rotavirus and epizootic hemorrhagic disease virus, Baltimore group III)), porcine respiratory & reproductive syndrome (Baltimore group IV), porcine epidemic diarrhea virus(Baltimore group IV), transmissible gastroenteritis virus (Baltimore group IV), Newcastle disease virus (Baltimore group V), influenza viruses (e.g., H5N1, Baltimore group V), human immunodeficiency virus (Baltimore group VI), and hepatitis viruses (e.g., hepatitis B virus, (Baltimore group VII).

The EO compositions described herein further provide indirect antiviral benefits. For example, EOs are known to be antibacterial and antifungal and have low cytotoxicity, and accordingly maintain or increase immune system strength. Additionally, these EO compositions combat bacterial which some viruses, such as MS1 bacteriophage, infect within a host animal. Because the administration methods of EO compositions can be integrated with existing captive and wild animal population procedures (e.g., feeding), costly and time intensive vaccination and pharmaceutical procures can be reduced or eliminated. In some embodiments, antiviral efficacy of an EO composition is enhanced by indirect antiviral benefits.

The EO fractions of embodiments disclosed herein are configured to provide an antiviral effect with low toxicity to the host subject or system. Further, such low toxicity is paired with an effect which generally enhances the health and immune system of a host subject, thereby providing a second antiviral effect stemming from the immune system of the host in addition to the antiviral effect of the EO composition. Some EOs provided herein are individually effective against one virus or a class of viruses. Some embodiments comprise a blend of two or more EOs in order to effect suitable antiviral efficacy against one virus or a class of viruses. Some embodiments comprise a blend of two or more EOs in order to effect suitable antiviral efficacy against a number of viruses in one or more viral classes.

Embodiments provided herein are effective against viruses belonging to the Baltimore group III, dsRNA viruses, in particular epizootic hemorrhagic disease of white-tailed deer (non-enveloped virus), and rotavirus (non-enveloped virus). Embodiments provided herein are effective against viruses belonging to the Baltimore group IV, (+)ssRNA viruses, in particular MS2 bacteriophage virus (non-enveloped virus), porcine respiratory and reproductive syndrome virus (enveloped virus), porcine epidemic diarrhea virus (enveloped virus), transmissible gastroenteritis coronavirus (enveloped virus), bovine viral diarrhea virus (enveloped virus), and dairy coronavirus (enveloped virus).

Figure 1:
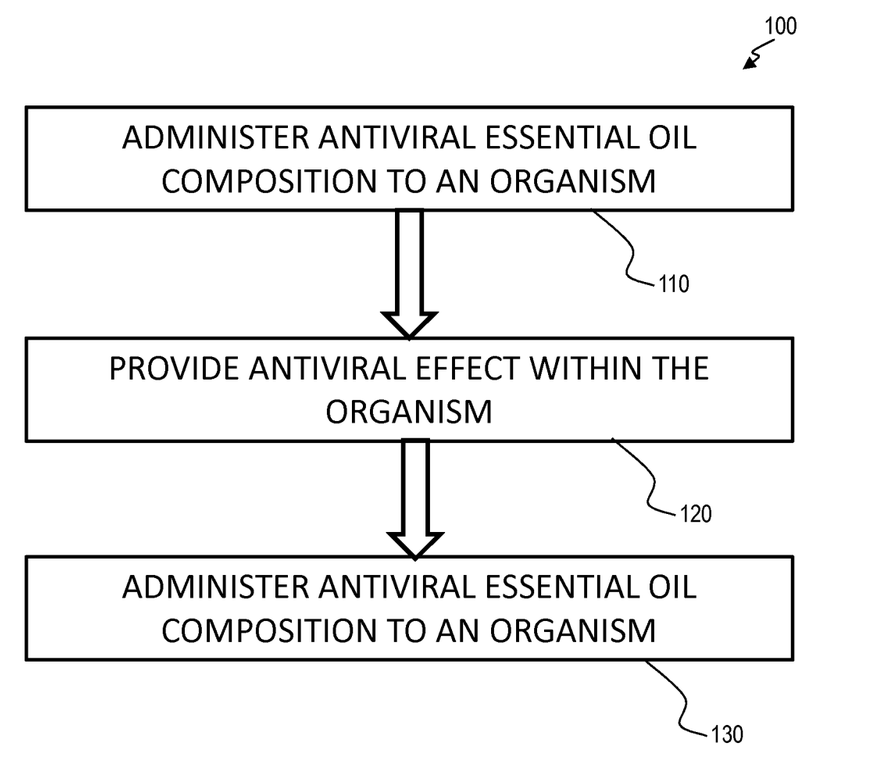
FIG. 1 illustrates a method for providing an antiviral effect within an organism, according to one or more embodiments of this disclosure.

FIG. 1 illustrates a method 100 for providing an antiviral effect within an organism that includes administering an antiviral EO composition to an organism 110 and providing an antiviral effect within the organism 120. Method 100 can optionally further comprise a subsequent administration 130 of an antiviral EO composition. Subsequent administration 130 can comprise one or more administrations. For example, subsequent administration 130 can comprise a daily administration, or an administration occurring a plurality of times within a day, for one or more days.

EO compositions as provided herein contain EOs derived from plants (i.e., "natural" EOs) and additionally or alternatively their synthetic analogues. Many embodiments comprise a combination of EOs. Some embodiments comprise a combination of natural and synthetic EOs. In some embodiments, synthetic EOs can be a "natures equivalent" synthetic blend, which generally mimics an EO assay of a natural EO by including at least 5, at least 10, at least 15, or at least 20 of the most critical EOs within a natural EO. A critical EO can be determined by weight percent, and/or by pharmacological efficacy. For example, a nature's equivalent synthetic oil can comprise the following constitutions as provided in Table 1:

TABLE 1

Nature's Equivalent Synthetic Thyme EO:

| Constituent | Wt. % |
| --- | --- |
| Thymol | 42.7-44.08 |
| para-Cymene | 26.88-27.09 |
| Linalool | 4.3-4.34 |
| alpha-Pinene | 4.1-4.26 |
| alpha-Terpineol | 3.14-3.14 |
| 1,8-Cineole | 2.82-3.01 |
| beta-Caryophellene | 1.98-2.27 |
| Limonene | 1.59-1.78 |
| delta-3-Carene | 1.3-1.41 |
| beta-Myrcene | 1.26-1.31 |
| Linalyl Acetate | 1.11-1.24 |
| beta-Pinene | 1.04-1.22 |
| Terpinen-4-ol | 0.96-1.14 |
| alpha-Caryophyllene | 0.71-0.71 |
| gamma-Terpinene | 0.7-0.7 |
| Sabinene | 0.37-0.5 |
| Borneol | 0.27-0.32 |
| Camphene | 0.13-0.17 |

An EO composition generally includes EOs from the classes of terpenes, terpenoids, phenylpropenes and combinations thereof. The EOs can include oils from one or more of the genus *Origanum*, the genus *Thymus*, and the genus *Cinnamomum*, and combinations thereof. In some embodiments, natural EOs are used which comprise, for example, 1-100 individual EOs. Oils derived from the genus *Thymus* can comprise 50 or more individual EOs. For example, *Thymus vulgaris* (common thyme) comprises about 40% monoterpene hydrocarbons, about 51% monoterpenes, about 6% sesquiterpene hydrocarbons, and about 1% oxygenated sequiterpenes, wherein some of the primary species can include about 30% to about 50% thymol, about 18% to about 31% para-cymene, about 2% to about 5% caryophyllen, about 1% to about 5% carvacrol, and about 2% to about 4% linalool. Oils derived from the genus *Origanum* can similarly comprise 50 or more individual EOs. For example, *Origanum vulgare* (common oregano) comprises about 60% to about 80% carvacrol, about 0% to about 13% linool, about 3% to about 9% para-cymene, about 2% to about 14% g-terpinene, about 0% to about 5% a-terpinene, about 0% to about 4% thymol, about 1% to about 2% myrcene, and about 0% to about 3% t-caryophyllene, among others.

Natural EOs derived from a particular species can comprise varying levels of constituent EOs based on climate, soil, and geographical location, among other factors. For example, *Thymus vulragis* endemic to France can comprise an EO fraction containing about 41% thymol, about 18% para-cymene, and about 13% g-terpinene, whereas *Thymus vulragis* endemic to Brazil can comprise an EC) fraction containing about 47% thymol, about 39% para-cymene, and about 0.3% g-terpinene. Different species of *Thymus* can similarly vary; for example, *Thymus serpyllum* can comprise an EO fraction containing only about 1% thymol. One of skill in the art will know from this disclosure that EOs derived from various species and derived from samples within a particular species which were grown in varying conditions can be blended.

Similarly, EOs can in some embodiments be used from outside a specified species, when such an EO source satisfies the requirements of a given embodiment. For example, an embodiment which calls for an *Origanum* EO assay having a weight percent of a particular constituent, such as carvacrol, a portion or all of the EO assay can comprise EO from *Levisticum officinale* (commonly lovage), *Monarda punctate* (commonly horsemint), *Monarda didyma* (commonly crimson beebalm), *Nigella sativa* (commonly fennel flower), or other sources capable of providing a suitable amount of carvacrol. Inter-species and inter-genus natural EO mixing is practicable provided that one or more EO sources do not contain detrimental constituent oils. A detrimental constituent oil is one which frustrates the purpose of a particular embodiment, for example, by increasing cytotoxicity to an unacceptable level or altering the taste of a composition such that an animal refuses to ingest the composition at a desired rate.

When two or more EOs are present in an embodiment, the amount of any individual EO can be from about 0.5%-99.5% of the EO fraction by weight. For example, if both thymol and cinnamaldehyde are present, the amount of thymol can be about 0.5%-99.5% and the cinnamaldehyde can be about 99.5% to about 0.5% of the oil fraction. The EO fraction can comprise up to 50% of an EO composition. In some embodiments, the EO fraction is diluted within an EO composition to less than about 1000 ppm, less than about 500 ppm, less than about 200 ppm, less than about 100 ppm, less than about 50 ppm, less than about 25 ppm, less than about 15 ppm or less than about 10 ppm.

In some embodiments, an EC) fraction comprises at least 10% phenolic terpenoids, at least 35% phenolic terpenoids, at least 60% phenolic terpenoids, at least 70% phenolic terpenoids, or at least 85% phenolic terpenoids. A phenolic terpenoid fraction can comprise a carvacrol to thymol ratio of about 1:2 to about 8:1, about 1:1 to about 7:1, or about 5:1 to about 6:1. Some such embodiments further comprises para-cymene. Para-cymene can be present within the EO fraction in about a 1:1 to about a 1:7 ratio with the phenolic terpenoid fraction. Some embodiments include an EO fraction comprising about 30% to about 80% carvacrol, about 10% to about 60% thymol, and about 10% to about 60% para-cymene. Some embodiments can include up to 50% of secondary natural EO constituents from one or more of the genus *Origanum* and the genus *Thymus*. Such embodiments are particularly efficacious against viruses belonging to Baltimore Classification groups III and IV.

In some embodiments an EOs fraction comprises about 50% to about 80% natural *Thymus* EO, and about 20% to about 50% phenylpropanoid. In this embodiment, the phenylpropanoid can comprise cinnamaldehyde. Such an embodiment can include about 0.1% to about 19.9% carvacrol, about 20% to about 39.9% thymol, about 10% to about 29.9% para-cymene. The embodiment can further comprise about 0% to about 19.9% secondary *Thymus* oil constituents. The *Thymus* oil can be present within the EO fraction an about a 2:1 to about a 1:3 ratio with the phenylpropanoid. Such embodiments are particularly efficacious against viruses belonging to Baltimore Classification groups III and IV.

The EOs present in some embodiments can include oils of plants from the Labiatae or Lamiaceae family, and the Lauraceae family, including hybrids of plants from one or both families. Suitable EOs from the Lauraceae family can comprise those from the *Cinnamomum* genus. Within the *Cinnamomum* genus, suitable species can include *Cinnamomum burmannii, Cinnamomum cassia, Cinnamomum carnphora, Cinnamomum loureiroi, Cinnamomum mercadoi, Cinnamomum oliveri, Cinnamomum osmophloeum, Cinnamomum ovalifolium, Cinnamomum parthenoxylon, Cinnamomum pedunculatum, Cinnamomum subavenium, Cinnamomum tamala, Cinnamomum verum, Cinnamomum verum,* and hybrids thereof. The species provided in this paragraph constitute a non-limiting list of suitable species within each genus, such suitability being highlighted, in part, to lend guidance to one of skill in the art for selecting additional suitable species from each respective genus.

Suitable EOs from the Lamiaceae family can comprise those from one or more of the *Thymus* genus, the *Origanum* genus, the *Monarda* genus. Within the *Thymus* genus, a non-limiting list of suitable species can include *Thymus caespititius, Thymus capitates, Thymus carnosus, Thymus citriodorus, Thymus glandulosus, Thymus Herba-borana, Thymus hyemalis, Thymus integer, Thymus pseudolanuginosus* (formerly *T. lanuginosus*), *Thymus mastichinia, Thymus montanus, Thymus moroderi, Thymus pannonicus, Thymus praecox, Thymus pulegioides, Thymus serpyllum, Thymus vulgaris, Thymus zygis*, and hybrids thereof. Within the *Origanum* genus, a non-limiting list of suitable species can include *Origanum amanum, Origanum compacturn, cordifolium, Origanum dictamnus, Origanum laevigatum, Origanum libanoticum, Origanum majorana, Origanum microphyllum, Origanum onites, Origanum rotundifolium, Origanum scabrum, Origanum syriacum, Origanum vulgare*, and hybrids thereof. Within the *Monarda* genus, a non-limiting list of suitable species can include *Monarda citriodora, Monarda clinopodioides, Monarda didyma, Monarda fistulosa, Monarda media, Monarda punctata*, and hybrids thereof. The species provided in this paragraph constitute a non-limiting list of suitable species within each genus, such suitability being highlighted, in part, to lend guidance to one of skill in the art for selecting additional suitable species from each respective genus.

The EOs present in some embodiments can further include lavender EOs from the *Lavandula* genus, Mexican bay leaf EOs from the *Liteas* genus (e.g., *L. glaucescens*), West Indian bay tree EOs from the *Pimenta* genus (e.g., *P. racemosa*), Indonesian bay leaf EOs from the *Syzygium* genus, bay laurel EOs from the *Laurus* genus (e.g., *L. nobilis*), California bay laurel EOs from the *Umbellularia* genus (e.g., *U. californica*), lemon grass EOs from the *Cymbopogon* genus (e.g., *C. ambiguous, C. citratus, C. flexuosus, C. martini, C. nardus, C. schoenanthus*), spearmint and peppermint EOs from the Mentha genus (e.g., *M. spicata, M. piperita*), rosemary EOs from the *Rosmarinus* genus (e.g., *R. officinalis*), sage EOs from the *Salvia* genus (e.g., *S. sclarea*), anise EOs from the *Pimpinella* genus (e.g., *P. anisum, P. cypria, P. major*, and *P. saxifraga*), ginger EOs from the *Zingiber* genus (e.g., *Z. barbatum, Z. mioga, Z. officinale, Z. zerumbet*, and *Z. spectabile*). bergamot EOs from the *Citrus* genus (e.g., *C. bergamia*), eucalyptus EOs from the *Eucalyptus* genus, melaleuca EOs from the *Melaleuca* genus, wintergreen EOs from the *Gaultheria* genus (e.g., *G. antipoda, G. appressa, G. cuneata, G. depressa, G. hispida, G. hispidula, G. humifusa, G. insipida, G. lanigera, G. leschenaultii, G. mucronata, G. nummularioides, G. oppositifolia, G. ovatifolia, G. procumbens, G. rupestris, G. shallon*, and *G. trichophylla*), cannabis EOs from the *Cannabis* genus, marjoram EOs from the *Origanum* genus (e.g., *O. majorana*, and *O. dictamnus*), orange EOs from the *Citrus* genus, rose EOs from the Rosa genus, hybrids thereof, and combinations thereof. The species provided in this paragraph constitute a non-limiting list of suitable species within each genus, such suitability being highlighted, in part, to lend guidance to one of skill in the art for selecting additional suitable species from each respective genus.

In some embodiments, an EO composition can include an EO fraction comprising two or more EOs from the Lauraceae family and/or the Lamiaceae family. In some embodiments, an EO composition can include an EO fraction comprising two or more of cinnamon EO from the *Cinnamomum* genus, thyme EO from the *Thymus* genus, and oregano EO the *Origanum* genus. In a specific embodiment, an EO composition can include an EO fraction comprising cinnamon EO from the *Cinnamomum* genus and thyme EO from the *Thymus* genus. In another specific embodiment, an EO composition can include an EO fraction comprising cinnamon EO from the *Cinnamomum* genus and oregano EO the *Origanum* genus. In another specific embodiment, an EC) composition can include an EO fraction comprising thyme EO from the *Thymus* genus and oregano EO the *Origanum* genus.

In some embodiments, an EO composition can include an EO fraction comprising synthetic cinnamaldehyde and one or more of thyme EOs from the *Thymus* genus and oregano EO from the *Origanum* genus. In a specific embodiment, an EO composition can include an EO fraction comprising synthetic cinnamaldehyde and thyme EO from the *Thymus* genus. In another specific embodiment, an EO composition can include an EO fraction comprising synthetic cinnamaldehyde and oregano EO the *Origanum* genus. In some embodiments, oregano EO can comprise carvacrol. Additionally or alternatively, thyme EO can comprise thymol.

In some embodiments, the EO fraction can comprise about 0% to about 50% oregano EO, about 0% to about 50% thyme EO, and about 0% to about 50% cinnamon EO. In other embodiments, the EO fraction can comprise about 15% to about 42.5% oregano EO, about 15% to about 42.5% thyme EO, and about 15% to about 42.5% cinnamon EO. In all such embodiments, cinnamon EO can optionally comprise synthetic cinnamaldehyde.

In some embodiments, the EO fraction can comprise about 0.5% to about 99.5% oregano EO and about 0.5% to about 99.5% thyme EO. In a specific embodiment, the EO fraction can comprise about 25% to about 75% oregano EO and about 25% to about 75% thyme EO. In another specific embodiment, the EO fraction can comprise about 40% to about 60% oregano EO and about 40% to about 60% thyme EO. In one specific embodiment, the EO fraction can comprise about 50% oregano EO and about 50% thyme EO.

In some embodiments, the EO fraction can comprise about 0.5% to about 99.5% oregano EO and about 0.5% to about 99.5% cinnamon EO. In a specific embodiment, the EO fraction can comprise about 25% to about 75% oregano EO and about 25% to about 75% cinnamon EO. In one specific embodiment, the EO fraction can comprise about 50% oregano EO and about 50% cinnamon EO. In another specific embodiment, the EO fraction can comprise about 50% to about 80% oregano EO and about 20% to about 50% cinnamon EO. In another specific embodiment, the EO fraction can comprise about 60% to about 70% oregano EO and about 25% to about 40% cinnamon EO. In one specific embodiment, the EO fraction can comprise about 66% oregano EO and about 33% cinnamon EO. In all such embodiments, cinnamon EO can optionally comprise synthetic cinnamaldehyde.

In some embodiments, the EO fraction can comprise about 0.5% to about 99.5% thyme EO and about 0.5% to about 99.5% cinnamon EO. In a specific embodiment, the EO fraction can comprise about 25% to about 75% thyme EO and about 25% to about 75% cinnamon EO. In one specific embodiment, the EO fraction can comprise about 50% thyme EO and about 50% cinnamon EO. In another specific embodiment, the EO fraction can comprise about 50% to about 80% thyme EO and about 20% to about 50% cinnamon EO. In another specific embodiment, the EO fraction can comprise about 60% to about 70% thyme EO and about 25% to about 40% cinnamon EO. In one specific embodiment, the EO fraction can comprise about 66% thyme EO and about 33% cinnamon EO. In all such embodiments, cinnamon EO can optionally comprise synthetic cinnamaldehyde.

Many EO compositions comprise an EO fraction comprising an effective amount of carvacrol, an effective amount of thymol, an effective amount of cinnamaldehyde, an effective amount of paracymene, or combinations thereof. In an EO composition including an EO fraction comprising oregano EO, thyme EO, and cinnamon EO, the EO fraction can comprise two or more natural EOs wherein the combined EOs comprise at least an effective amount of carvacrol, at least an effective amount of thymol, and at least an effective amount of cinnamaldehyde. Suitable EOs can include EOs from the *Cinnamomum* genus, EOs from the *Origanum* genus, EOs from the *Thymus* genus, EOs from the *Monarda* genus (e.g., *M. citriodora, M. clinopodioides, M. didyma, M. fistulosa, M. media, M. punctata*), EOs from the *Trachysperrnum* genus (e.g., *T. ammi*), EOs from the *Nigella* genus (e.g., *N. sativa*), and combinations thereof. Other EOs can be used such that effective amounts of carvacrol, thymol, paracymene, and cinnamaldehyde are achieved in the EO fraction. Such a composition comprising natural EOs can be supplemented by one or more synthetic EOs to achieve effective amounts of carvacrol, thymol, paracymene, and cinnamaldehyde.

In an EO composition including an EO fraction comprising two or more of oregano EO, thyme EO, and synthetic cinnamaldehyde, the EO fraction can comprise one or more natural EOs and synthetic cinnamaldehyde, wherein the combined EOs and synthetic cinnamaldehyde comprise at an effective amount of two or more of carvacrol, at least an effective amount of thymol, and at least an effective amount of cinnamaldehyde. Suitable EOs can include EOs from the *Cinnamomum* genus, EOs from the *Origanum* genus, EOs from the *Thymus* genus, EOs from the *Monarda* genus (e.g., *M. didyma*, and *M. fistulosa*), EOs from the *Trachyspermum* genus (e.g., *T. ammi*), EOs from the *Nigella* genus (e.g., *N. sativa*), and combinations thereof. Still other natural EOs can be used such that effective amounts of two or more of carvacrol, thymol, and cinnamaldehyde are achieved in the EO fraction.

Some EO compositions comprise an EO fraction comprising one or more of an effective amount of thymol, an effective amount of paracymene, an effective amount of carvacrol, or an effective amount of cinnamaldehyde. An effective amount of thymol can comprise at least about 5 wt. %, at least about 10 wt. %, at least about 15 wt. %, at least about 18 wt. %, at least about 20 wt. %, or at least about 25 wt. % of the EO fraction. In some embodiments, an effective amount of thymol can comprise up to about 10 wt. %, up to about 15 wt. %, up to about 18 wt. %, up to about 20 wt. %, up to about 35 wt. %, or up to about 50 wt. % of the EO fraction. An effective amount of paracymene can comprise at least about 5 wt. %, at least about 10 wt. %, at least about 15 wt. %, at least about 18 wt. %, at least about 20 wt. %, or at least about 25 wt. % of the EO fraction. In some embodiments, an effective amount of paracymene can comprise up to about 10 wt. %, up to about 15 wt. %, up to about 18 wt. %, up to about 20 wt. %, up to about 35 wt. %, or up to about 50 wt. % of the EO fraction. An effective amount of carvacrol can comprise at least about 10 wt. %, at least about 25 wt. %, at least about 40 wt. %, at least about 55 wt. %, at least about 60 wt. %, or at least about 65 wt. % of the EO fraction. In some embodiments, an effective amount of carvacrol can be less than 1 wt. %. An effective amount of cinnamaldehyde can comprise at least about 10 wt. %, at least about 15 wt. %, at least about 20 wt. %, at least about 25 wt. %, at least about 30 wt. %, at least about 33 wt. %, or at least about 40 wt. %, of the EO fraction. In some embodiments, an effective amount of cinnamaldehyde can comprise up to about 10 wt. %, up to about 15 wt. %, up to about 20 wt. %, up to about 25 wt. %, up to about 30 wt. %, up to about 33 wt. %, or up to about 40 wt. %, of the EO fraction.

In some embodiments, oregano EO can be replaced by one or more oils which include at least 45 wt. % carvacrol, at least 55 wt. % carvacrol, at least 65 wt. % carvacrol, or at least 75 wt. % carvacrol. In some embodiments, thyme EO can be replaced by one or more oils which include at least 30 wt. % thymol, at least 35 wt. % thymol, at least 40 wt. % thymol, or at least 45 wt. % thymol. In some embodiments, thyme EO can be replaced by one or more oils which include at least 30 wt. % paracymene, at least 35 wt. % paracymene, at least 40 wt. % paracymene, or at least 45 wt. % paracymene. In some embodiments, cinnamon EO can be replaced by one or more oils which include at least 35 wt. % cinnamaldehyde, at least 40 wt. % cinnamaldehyde, at least 50 wt. % cinnamaldehyde, or at least 75 wt. % cinnamaldehyde. Suitable sources of effective amounts of carvacrol, thymol, and/or cinnamaldehyde can include natural EOs and/or synthetic EOs.

EO compositions can further comprise one or more of an effective amount of eugenol, or an effective amount of citronella. An effective amount of eugenol can comprise at least about 5 wt. %, at least about 7.5 wt. %, at least about 10 wt. %, or at least about 12.5 wt. % of the EO fraction. An effective amount of citronella can comprise at least about 5 wt. %, at least about 7.5 wt. %, at least about 10 wt. %, or at least about 12.5 wt. % of the EO fraction.

In some embodiments, the EO fraction comprises 100% of the EO composition. An EO composition can optionally comprise a carrier. Carriers are ideally inert materials which do not react with the active components (i.e., the EO fraction) of the composition chemically, or bind the active components physically by adsorption or absorption. Liquid carriers include water, pure water, such as reverse osmosis water, or other liquids such as crop oils or surfactants which pharmacologically suitable for a subject or system. Liquid carriers can include liquid animal feeds such as milk. In some embodiments, the composition will be about 80% to about 99% liquid carrier, about 70% to about 99% liquid carrier, about 60% to about 99% liquid carrier, or about 40% to about 99% liquid carrier.

Solid carriers such as limestone and diatomaceous earth can be utilized. Solid carriers can be utilized for practical purposes, such as machinery used to coat seeds with EO compositions or distribute EO compositions into a field. Solid carriers can include animal feeds, such as wheat, barely, or hay. Animal feeds can include trace nutrient packs, such as chelated metals. In some embodiments the composition can be at least about 30% solid carrier by weight, at least about 55% solid carrier by weight, at least about 75% solid carrier by weight, or at least about 80% solid carrier. In some embodiments, the composition will be about 80% to about 99% solid carrier, about 70% to about 99% solid carrier, about 60% to about 99% solid carrier, or about 40% to about 99% solid carrier.

The total amount of carrier in a composition can be determined based on a ratio of one or more carriers to one or more elements within the composition. In some examples, a particular ratio or ratio range of one or more carriers to elements within the composition can be determined based on an animal's antiviral treatment dosage, nutritional needs, or palatability of the EO composition for a particular consuming animal.

EO compositions disclosed herein can provide an antiviral effect in humans, and ruminant and non-ruminant animals. Animals can include mammals, equine, bovine, swine, deer, fowl, and aquatics such as fish and shrimp. In some embodiments, EO compositions are configured to a particular administration method. EO composition administration methods can include oral administrations in combination with solids or liquids, oral administration in the form a capsule, tablet, or bolus, epidermal administration in the form of a lotion, ointment or cream, inhalant administration, mucosal membrane administrations, pessary administrations, and suppository administrations. Preference for a given administration method can vary on a number of conditions. For example, feed administration can be preferred to water-line administration as it may ensure a higher probability of composition dose ingestion. Administration methods such as solid feed and water line can be used to iteratively deliver the antiviral EO compositions described herein.

In some instances, combinations of administration methods are preferable. In such cases, different EC) compositions can be utilized by each respective administration method. For example, a feed administration can be paired with a bolus administration, wherein the concentration of an EO fraction in the feed administration composition is lower than the concentration of an EO fraction in the bolus administration composition. Embodiments can be configured to accommodate an animal's palate. In one embodiment, the carvacrol fraction of an EO composition can be reduced to below a threshold level above which an animal may refuse to ingest a dose. For example, swine feed thresholds can be 15 ppm carvacrol in feed, and fowl feed thresholds can be 7.5 ppm carvacrol in feed. Threshold levels can be much higher for one-time or short duration feed schedules. In other embodiments, one or more additional EC) constituents, such as cinnamaldehyde, can be included to effect proper viral coverage.

The compositions can be prepared using carriers. Carriers are ideally inert materials which do not react with the active components of the composition chemically, or bind the active components physically by absorption or adsorption. Typically the primary purpose of a carrier is to facilitate administration. Liquid carriers include pure water, such as reverse osmosis water, or other liquids such as milk, colostrum, crop oils or surfactants which are compatible with the composition and the animal identified to consume the composition. Solid carriers can include limestone ($CaCO_3$), silicon dioxide, zeolite, commercial nutrient products, agricultural feed, meat and fish meal, and bone meal. Feed can be liquid, solid, or any other form of feed known to those of skill in the art. For example, feed can comprise milk, or other heterogeneous liquid feeds such as a grain and/or protein slurry. Feed can include solid matter such as barley, corn, soy, oats, or hay. When solid matter is utilized as a carrier, the antiviral agent can comprise a powder, or can be emulsified in a liquid. In some embodiments, the carrier is tailored to habitat or ecological considerations in order to ensure or enhance administration efficacy in a certain population or species of subjects. For example, a carrier can comprise salt in the form of a salt lick, such that deer are effectively administered an antiviral agent without interference or depletion of the antiviral agent by other organisms. In some embodiments, carriers provide a non-essential benefit, such as a nutritional benefit. For example, limestone acts as calcium source when used as a solid carrier in a feed embodiment. In other embodiments a carrier is chosen for compatibility with a composition administration method. Diatomacoues earth, xeolite, and limestone are suitable carriers for solid feed. Vegetable oils such as olive oil and soy oil are suitable carriers for topical administrations, such as for compositions applied to an udder. Compounds such as sugars (e.g., dextrose and maltodextrin), limestone, diatomaceous earth, and arabinogalactan are suitable carriers for capsule embodiments. In some embodiments, a carrier is used to dilute the EC) fraction within an EO composition to less than about 1000 ppm, less than about 500 ppm, less than about 200 ppm, less than about 100 ppm, less than about 50 ppm, less than about 25 ppm, less than about 15 ppm or less than about 10 ppm. In other embodiments, the EO fraction can have up to a 1:1 ratio with the carrier, up to a 2:1 ratio with the carrier, or up to a 5:1 ratio with the carrier.

An EO composition can further comprise one or more emulsifiers. An emulsified EO fraction can increase the bioavailability and antiviral efficacy of an EO composition when administered to a subject or a system. Emulsifiers allow an EO fraction to evenly disperse throughout an inorganic carrier such as water and can further improve dose administration accuracy. Emulsifiers also make EOs less volatile within a composition. An EO fraction can be combined only with an emulsifier, without a carrier. An EO fraction can be combined with an emulsifier and a dry carrier, or alternatively an EO fraction can be combined with an emulsifier and a liquid carrier, as disclosed above, to form an emulsion. The emulsifier can be combined with an EO fraction in a ratio of about 3:1 to about 1:3, about 2:1 to about 1:2, about 1.5:1 to about 1:1.5, or about 1:1. An EO composition comprising an EO fraction, a liquid carrier, and an emulsifier can have an average EO droplet size of less than about 25 microns, less than about 15 microns, less than about 10 microns or less than about 5 microns.

An emulsifier combined with a liquid carrier can generally be referred to as a liquid emulsifier. In some embodiments, an emulsion can comprise up to about 35%, up to about 40%, up to about 45%, or up to about 50% EO fraction and emulsifier, with the balance comprising a liquid carrier. In some embodiments, an emulsion can comprise less than about 20%, less than about 15%, less than about 10%, about 5%, or less than about 5% EO fraction and emulsifier, with the balance comprising a liquid carrier. In some embodiments, an emulsion can comprise about 40% to about 60%, or about 45% to about 55% EO fraction and emulsifier, with the balance comprising a liquid carrier. In some embodiments, an emulsion can comprise about 1% to about 10%, about 2.5% to about 7.5%, or about 5% EO fraction and emulsifier, with the balance comprising a liquid carrier. In many embodiments the liquid carrier is water. The liquid carrier content can vary depending on the amount and type of emulsifier.

In some instances, organic solvents are additionally or alternatively used in place of liquid carriers such as water or other liquid carriers described above. Organic solvents can include C1-C12 alcohols, diols, triols, dialkyl phosphate, tri-alkyl phosphate (e.g., tri-n-butyl phosphate), semi-synthetic derivatives thereof, and combinations thereof. Specifically, organic solvents can include ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof. However, such organic solvents are at a minimum detrimental, if not toxic, to host subjects including animals and humans, and therefore are not suitable for use in the antiviral EO compositions described herein. Accordingly, in some embodiments, antiviral EO compositions can comprise no organic solvents.

A suitable emulsifier is larch arabinogalactan. Other suitable emulsifiers include tannin compounds. Other suitable emulsifiers include polydextrose, chitin, psyllium, methylcellulose, hydrolyzed guar, guar gum, guar gum derivatives, soy polysaccharide, oat bran, pectin, inulin, Fructooligosaccharides (FOS), xanthan gum, alginate, chemically modified cellulosic, Acacia, and gum Arabic. One or more emulsifiers can be used to form an emulsion. In some embodiments, one or more emulsifiers can additionally or alternatively be used as a stabilizer. Stabilizers can be used to alter the viscosity of an emulsion. Altering a viscosity can include maintaining a viscosity, increasing a viscosity, or decreasing a viscosity. Generally, high molecular weight polysaccharides can act as stabilizers. Additionally, when arabinogalactan and/or tannin compounds are used as emulsifiers, the remaining above listed emulsifiers can additionally be used to stabilize, or increase the viscosity, of an EO composition. An advantage of arabinogalactan is the ability to form a suitable emulsion without an organic solvent.

In some embodiments, a suitable emulsifier can include a tannin compound, such as tannic acid. Tannin can be used as an alternative to or in combination with the emulsifiers described above. Tannin compounds can provide better stability, anti-microbial properties and stabilizing characteristics than traditional EO emulsifiers. In some embodiments, a liquid emulsifier can comprise about 100% tannic acid, about 80% to about 95% tannic acid, about 60% to about 85% tannic acid, about 40% to about 60% or about 1% to about 50% tannic acid, with the balance being a liquid carrier. An advantage of tannin compounds is the ability to form a suitable emulsion without an organic solvent.

Arabinogalactan and tannin compounds are particularly suitable for use as emulsifiers as they exhibit low cytotoxicity, are palatable to animals, and facilitate small EO droplet sizes (e.g., than about 25 microns, less than about 15 microns, less than about 10 microns or less than about 5 microns). Arabinogalactan and tannin compounds are suitable emulsifiers individually or in combination. When both are present, the ratio of arabinogalactan to tannin compounds of a total amount of emulsifier in an EO composition can be about 1:10, about 3.5:10, about 1:2, about 6.5:10, about 9:10, about 1:1, about 10:9, about 10:6.5, about 2:1, about 10:3.5, or about 10:1. An advantage of arabinogalactan and tannin compounds used in combination as emulsifiers is the ability to form a suitable emulsion without an organic solvent.

A method of making an EO composition, such as an EO emulsification in an aqueous carrier, can comprise agitating one or more liquid emulsifiers, contacting the one or more liquid emulsifiers with one or more EOs sufficient to create an emulsion. The emulsion can be agitated while monitoring at least an emulsion temperature. The liquid emulsifier (i.e., water and one or more emulsifiers) can be agitated in a vessel, such as by stirring, for a time sufficient to produce visible motion on the surface of the one or more liquid emulsifiers. The visible motion can be from the approximate surface center to one or more surface edges, at the perimeter of the vessel, for example. The time taken to reach such visible motion can depend on the type of liquid emulsifier and ratio of emulsifier to water (e.g., viscosity). Once a suitable motion is established at the surface of the liquid emulsifier, one or more EOs can be added. After continued agitation of the liquid, an emulsion can form. The contact rate or addition rate should be slow enough to substantially prevent volatilization of the EOs.

Agitation can continue during the addition of the EOs. Addition of EOs should be slow enough to prevent a high shear environment, adversely affecting the volatilization of the oils and preventing formation of a suitable emulsion. Agitation of the emulsion can continue until the emulsion temperature reaches a temperature near, but below, a volitization temperature. Such a temperature can include about 100° F. to about 110° F., about 103° F. to about 108° F. or about 104° F. to about 107° F. for emulsions containing one or more of thyme EO, oregano EO, or cinnamon EO. Viscosity typically increases as the emulsion forms. The method of agitation can be adjusted to compensate for the increase in viscosity. For example, if a stirring method is used, the stirrer or paddle can increase in force to maintain the same level of movement of the liquid as the emulsion thickens. The final emulsion can have an average droplet size of less than about 25 microns, less than about 15 microns, less than about 10 microns or less than about 5 microns. The smaller droplet size allows for a more stable emulsion and one that previously could not be utilized for antiviral uses due to instability and high volatilization rates. Nulling an emulsion can further include adding a stabilizer to the emulsion.

Antiviral EO compositions as described herein can provide antioxidant properties to a subject or host system. Antioxidants can enhance neutrophil function, improve fertility, reduce heat stress related pregnancy losses, reduce frequency of retained placentas, and reduce metritis in dairy cows. Oxygen radical absorbance capacity (ORAC) is the ability of a compound or composition to act as a proton donor and reducing agent for oxygen radicals. In particular, ORAC measures the ability of a compound or composition to act as a reducing agent for peroxyl radicals, hydroxyl radicals, peroxynitrite, superoxide anion, and singlet oxygen, the five most damaging oxygen radicals.

EXAMPLES

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

In the examples, "Synergy Essence" refers to an EO composition comprising about 60.4% carvacrol, about 10.8% thymol, about 9.9% paracymene, and about 18.9% secondary natural EO constituents. Some embodiments comprise Synergy Essence in combination with arabinogalactan. "REGANO 4XL" refers to an EO composition comprising about 67.9 wt. % RO water, 12.75 wt. % commercial product Larafeed powder (Larch tree arabinogalactan) extract, 0.60 wt. % TIC gum, and 18.75 wt. % EOs. The EOs fraction comprised a combination of 50% oregano oil and 50% thyme oil (60.4 wt. % carvacrol, 10.8 wt. % thymol, 9.9 wt. % paracymene, and 18.9 secondary oil constituents from oregano oil and thyme oil). RALCO SELECT, comprising 67.9 wt. % RO water, 12.75 wt. % commercial product Larafeed powder (Larch tree arabinogalactan) extract, 0.60 wt. % TIC gum, and 18.75 wt. % EOs. The EOs fraction comprised 66.66% thyme oil (0.13% wt. % carvacrol, 30.5 wt. % thymol, 18.0 wt. % para-cymene, 18.0 wt. % other secondary thyme oil constituents) and 33.33% synthetic cinnamaldehyde. Ralco commercial product REGANO 4TL, comprising 58.53 wt. % RO water, 3.38 wt. % commercial product Larafeed powder (Larch tree arabinogalactan) extract, 0.60 wt. % TIC gum, 18.75 tannin emulsifier, and 18.75 wt. % EOs. The EOs fraction comprised 60.4 wt. % carvacrol, 10.8 wt. % thymol, 9.9 wt. % para-cymene, and 18.9% secondary oil constituents from oregano oil and thyme oil. Ralco commercial product REGANO EX, comprising 90 wt. % carrier (~75 wt. % limestone), 2.5 wt. % RO water, 2.5 wt. % commercial product Larafeed solids (Larch tree arabinogalactan), and 5 wt. % EOs. The EOs fraction comprised 20% thyme oil and 80% oregano oil, with a total assay of 60 wt. % carvacrol, 11 wt. % thymol, 10 wt. % para-cymene, 19.0 wt. % other secondary thyme oil constituents.

In each of Examples 1-4 and 6-15, the ASTM E1052 test method was used, which determines the virucidal efficacy of a biocide against a test virus in suspension. Generally, the ASTM E1052 method includes optionally loading the test virus with organic soil, and contacting the test virus with a test product at one or various levels of dilution at a ratio of 1 part virus+9 parts test product. After contacting, an aliquot is removed, neutralized, and assayed for the presence of the virus. Virus control, cytotoxicity, neutralization, and sterility controls are performed in parallel, and assayed concurrently with neutralized test suspensions. Tests and controls are each replicated twice. Following neutralization, the suspensions were enumerated using standard cell culture (e.g. $TCID_{50}$) or plaque assay techniques. Viral and cytotoxicity titers ($TCID_{50}/TCLD_{50}$ and $TCCD_{50}$, respectively) were determined according to the method developed by Spearman-Karber:

$$-(\text{Log}_{10} \text{ of } 1st \text{ Dilution}) - \left(\frac{\text{sum of \% mortality at each dilution}}{100}\right) - .05$$

Percent Reduction of Virus is determined according to the following formula:

$$\% \text{ Reduction} = 1 - \left(\frac{A}{B}\right) * 100$$

where: B=average $\text{Log}_{10}$ of virus control suspension, and A=average $\text{Log}_{10}$ of virus test suspension.

A weakness of the ASTM E1052 suspension time-kill method is the designated mix ratios for testing (1 part virus+9 parts germicide), which imparts dilution effects that may artificially lower product efficacy, thereby underestimating the same for certain actual application conditions (e.g., viral inactivation within a living animal). The ASTM E1052 method is also limited by a single dose iteration, the results of which underestimate antiviral efficacy of a multiple dose treatment method.

Example 1

Anti-viral Efficacy EO Composition Against Epizootic Hemorrhagic Disease Virus (Strain ATCC VR-982)

In this trial, the antiviral effectiveness of REGANO 4XL against EHDV was determined. The REGANO 4XL was diluted with water at various levels and mixed at a 9:1 ratio with the viral inoculum to achieve test systems having an EO fraction of 50 ppm. The viral inoculum target was 6.00 $\text{Log}_{10}$ upon combination with the REGANO 4XL. Permissive host cell line used for all trials was Vero ATCC CCL-81. Contact time between the viral inoculum and EO composition included 10 minutes and 30 minutes at 20.7° C. Results indicated no appreciable cytotoxicity. Viral and cytotoxicity titers ($TCID_{50}/TCLD_{50}$ and $TCCD_{50}$, respectively) results are given in Table 1 below:

TABLE 1

Anti-viral Efficacy of an EO Composition against EHDV

| | Contact Time (Minutes) | Suspension Type | $\text{Log}_{10}$ per 0.1 ml | Mean $\text{Log}_{10}$ per Suspension | % Reduction vs. Time Zero | $\text{Log}_{10}$ Reduction vs. Time Zero |
|---|---|---|---|---|---|---|
| Epizootic Hemorrhagic Disease Virus | Time Zero | Control | 5.00 4.25 | 4.63 | N/A | N/A |
| | 10 | Test | 4.75 4.00 | 4.38 | 43.77% | 0.25 |
| | 30 | Test | 3.75 4.00 | 3.88 | 82.22% | 0.75 |

In this trial, the antiviral effectiveness of REGANO 4XL against EHDV was determined. The REGANO 4XL was diluted with water at various levels and mixed at a 9:1 ratio with the viral inoculum to achieve test systems having EO fractions of 52 ppm, 104 ppm, and 208 ppm. The target viral inoculum was 6.00 $\text{Log}_{10}$ upon combination with the REGANO 4XL. Contact time varied per sample concentration, as shown in Table 2, with an organic soil load of 5% FBS. No appreciable cytotoxicity was observed. Results are shown in Table 2.

TABLE 2

Antiviral Effects of EO Compositions Against EHDV

| | Formulation Concentration | Contact Times | Suspension Type | $Log_{10}$ per 0.1 ml | % Reduction vs Time Zero | $Log_{10}$ Reduction vs Time Zero | % Reduction vs Timed Control | $Log_{10}$ Reduction vs Timed Control |
|---|---|---|---|---|---|---|---|---|
| Epizootic Hemorrhagic Disease Virus | N/A | Time Zero | Control | 5.50 | N/A | N/A | N/A | |
| | | 10 Minutes | | 5.50 | None | | | |
| | | 30 Minutes | | 5.25 | 43.77% | 0.25 | | |
| | | 60 Minutes | | 5.50 | None | | | |
| | | 120 Minutes | | 5.50 | None | | | |
| | 52 ppm | 60 Minutes | Test | 5.50 | None | | None | |
| | | 120 Minutes | | 5.00 | 68.38% | 0.50 | 68.38% | 0.50 |
| | 104 ppm | 30 Minutes | Test | 5.25 | 43.77% | 0.25 | 0.00% | 0.00 |
| | | 60 Minutes | | 5.00 | 68.38% | 0.50 | 68.38% | 0.50 |
| | 208 ppm | 10 Minutes | Test | 5.50 | None | | None | |
| | | 30 Minutes | | 5.00 | 68.38% | 0.50 | 43.80% | 0.25 |

Example 2

Anti-viral Efficacy of EO Composition Against MS-2 Bacteriophage Virus

In this trial, the antiviral effectiveness of REGANO 4XL against MS-2 bacteriophage virus was determined. The REGANO 4XL was diluted with water and mixed at a 9:1 ratio with the viral inoculum to achieve a test system having an EO fraction of 50 ppm. The viral inoculum target was ~7.5×10$^5$ plaque forming units (PFU) per ml, or 5.55 $Log_{10}$ per ml upon combination with the REGANO 4XL. Permissive host cell line used was *Escherichia coli*. Contact time between the viral inoculum and EO composition included 5 minutes and 10 minutes. Results indicated no appreciable cytotoxicity. The log 10 and percent reductions achieved by the test materials against MS-2 bacteriophage are given in Table 3:

TABLE 3

Modfied ASTM E1052 Suspension Time-Kill Test Data

| Substance | | Contact Time | PFU/ml | Geometric Mean PFU/ml | $Log_{10}$ per ml | $Log_{10}$ Reduction vs Time Zero | % Reduction vs Time Zero |
|---|---|---|---|---|---|---|---|
| MS-2 Coliphage | PBS (Control) | Time Zero | 3.49E+05 3.63E+05 | 3.56E+05 | 5.55 | N/A | N/A |
| | Regano 4XL (50 ppm) | 5 Minutes | 2.75E+05 2.95E+05 | 2.85E+05 | 5.45 | 0.10 | 20.00% |
| | | 10 Minutes | 2.25E+05 1.90E+05 | 2.07E+05 | 5.32 | 0.24 | 41.90% |

Example 3

Anti-viral Efficacy of EO Composition Against Porcine Epidemic Diarrhea Virus (Colorado 2013 Isolate Strain)

In this trial, the antiviral effectiveness of REGANO 4XL against PEDV was determined. The REGANO 4XL was diluted with water at various levels and mixed at a 9:1 ratio with the viral inoculum to achieve test systems having EO fractions of 50 ppm, 100 ppm, and 200 ppm. Permissive host cell line used for all trials was Vero 76. Contact time between the viral inoculum and each concentration of EO composition was 30 minutes with no organic soil load. No appreciable cytotoxicity was observed. An observed 0.25 log 10 reduction in viral titer demonstrated a 43.8% reduction for the 50 ppm test concentration. A 0.25 log 10 reduction in viral titer demonstrated a 43.8% reduction for the 100 ppm test concentration. A 0.25 log 10 reduction in viral titer demonstrated a 43.8% reduction for the 200 ppm test concentration.

REGANO 4XL was further tested at increased concentrations and extended contact times. The REGANO 4XL was diluted with water at various levels and mixed at a 9:1 ratio with the viral inoculum to achieve test systems having EO fractions of 50 ppm, 100 ppm, 200 ppm, 500 ppm, and 1000 ppm. Contact time was varied for each concentration, all samples maintained at 20.0° C. with no organic soil load. No appreciable cytotoxicity was observed. Results are given in Table 4.

TABLE 4

Effects of EO Compositions against PEDV

| | 50 ppm 4 Hours | 100 ppm 4 Hours | 200 ppm 2 Hours | 500 ppm 1 Hour |
|---|---|---|---|---|
| TCID50/200 µL | $10^{5.25}$ | $10^{5.25}$ | $10^{5.25}$ | $10^{6.00}$ |
| Log reduction | No reduction | No reduction | 0.50 $log_{10}$ | No reduction |
| % Reduction | No reduction | No reduction | 68.4% | No reduction |

REGANO 4XL was further tested with increased concentrations at lower contact times. The REGANO 4XL was diluted with water at various levels and mixed at a 9:1 ratio with the viral inoculum to achieve test systems having EO fractions of 200 ppm, 500 ppm, and 1000 ppm. Contact time between the viral inoculum and the EO compositions was 60 minutes, 30 minutes, and 30 minutes for the 200 ppm, 500 ppm and 1000 ppm trials, respectively. No appreciable cytotoxicity was observed. Results are given in Table 5.

TABLE 5

Effects of EO Compositions against PEDV

| | 200 ppm 60 Minute | 500 ppm 30 Minute | 1000 ppm 30 Minute |
|---|---|---|---|
| $TCID_{50}/200\ \mu L$ | $10^{5.50}$ | $10^{6.00}$ | $10^{2.00}$ |
| Log reduction | $0.50\ \log_{10}$ | No reduction | $4.00\ \log_{10}$ |
| Percent Reduction | 68.4% | No reduction | 99.99% |

Example 4

Anti-viral Efficacy EO Compositions Against Porcine Respiratory & Reproductive Syndrome (Strain NVSL, from the University of Kentucky)

In this trial, the antiviral effectiveness of a bay leaf EO composition, a cinnamon leaf EO composition, REGANO 4XL, and REGANO 4TL against PRRS were determined. The bay leaf EO composition comprised about 67.9 wt. % RO water, 12.75 wt. % commercial product Larafeed powder (Larch tree arabinogalactan) extract, 0.60 wt. % TIC gum, and 18.75 wt. % bay leaf EO (about 25.19 wt. % myrcene, 2.73 wt. % D-limonen, 1 wt. % paracymene, 2.17 wt. % linalool, 1.01 wt. % methyl euganol, 47.22 wt. % euganol, 10.8 wt. % chavicol, and 9.88 wt. % secondary constituent EOs.) The bay leaf EO composition substituted bay leaf EO for cinnamon leaf EO (about 1.08 wt. % alpha pinene, 1.12 wt. % alpha phellandrene, 2.4 wt. % linelool, 3.37 wt. % beta caryophyllene, 1.02 wt. % safrole, 1.37 wt. % cinnamaldehyde, 1.83 wt. % cinnamyl acetate, 80.67 wt. % eugenol, 1.96 wt. % eugenol acetate, and 5.18 wt. % secondary constituent EOs). The bay leaf and cinnamon EO compositions were each diluted with water and mixed at a 9:1 ratio with the viral inoculum to achieve test systems having EO fractions of 50 ppm. The $TCID_{50}$ viral inoculum target was $10^{5.50\ per}$ 100 µl upon combination with the EO composition. Permissive host cell line used in all trials was MARC-145. Contact time between the viral inoculum and the EO compositions was 30 minutes at 22.0° C. Organic soil load was 1% LBS. No appreciable cytotoxicity was observed. Results are given in Table 6.

TABLE 6

Effects of EO Compositions against PRRS Virus

| Dilution | Virus Control | Bay Leaf Essential Oil | Cinnamon Leaf Oil |
|---|---|---|---|
| TCID50/100 µL | 105.50 | 105.50 | 106.00 |
| Percent Reduction | NA | No Reduction | No Reduction |
| Log Reduction | NA | No Reduction | No Reduction |

Next, RALCO SELECT was diluted with water and mixed at a 9:1 ratio with the viral inoculum to achieve a test system having an EO fraction of 55.55 ppm. Contact time was 30 minutes at 20.0° C. Organic soil load was 1% LBS. No appreciable cytotoxicity was observed. Results are given in Table 7.

TABLE 7

Antiviral Effects of EO Composition Against PRRS Virus

| Dilution | Virus Control | Ralco Select | Cytotoxicity Control Ralco Select | Neutralization Control Ralco Select |
|---|---|---|---|---|
| TCID50/100 µL | $10^{6.00}$ | $10^{5.75}$ | $\leq 10^{1.50}$ | Neutralized at $\leq 1.50\ Log_{10}$ |
| Percent Reduction | NA | 43.8% | NA | NA |
| Log Reduction | NA | $0.25\ Log_{10}$ | NA | NA |

Next, REGANO 4XL was diluted with water and mixed at a 9:1 ratio with the viral inoculum to achieve a test system having an EO fraction of 50 ppm. Contact time was 30 minutes at 20.0° C. with an organic soil load of 1% FBS. No appreciable cytotoxicity was observed. Results are given in Table 8.

TABLE 8

Antiviral Effects of EO Composition Against PRRS

| Dilution | Virus Control | Regano 4XL | Cytotoxicity Control Regano 4XL | Neutralization Control Regano 4XL |
|---|---|---|---|---|
| TCID50/100 µL | $10^{6.25}$ | $10^{5.75}$ | $\leq 10^{1.50}$ | Neutralized at $\leq 1.50\ Log_{10}$ |
| Percent Reduction | NA | 68.4% | NA | NA |
| Log Reduction | NA | $0.50\ Log_{10}$ | NA | NA |

Next, REGANO 4TL was diluted with water and mixed at a 9:1 ratio with the viral inoculum to achieve a test system having an EO fraction of 50 ppm. Contact time was 30 minutes at 20.0° C. with an organic soil load of 1% FBS. No appreciable cytotoxicity was observed. Results are given in Table 9.

TABLE 9

Antiviral Effects of EO Composition Against PRRS Virus

| Dilution | Virus Control | Regano 4TL | Cytotoxicity Control Regano 4TL | Neutralization Control Regano 4TL |
|---|---|---|---|---|
| TCID50/100 µL | $10^{5.75}$ | $10^{5.25}$ | $\leq 10^{1.50}$ | Neutralized at $\leq 1.50\ Log_{10}$ |
| Percent Reduction | NA | 68.4% | NA | NA |
| Log Reduction | NA | $0.50\ Log_{10}$ | NA | NA |

Example 5

Anti-viral Efficacy of EO Compositions Against Porcine Epidemic Diarrhea Virus (PEDV)

In this trial, the antiviral effectiveness of an EO composition against porcine epidemic diarrhea virus (PEDV) was field-tested on a 900 sow farm. REGANO EX was fed to the sows at 0.75 lbs per ton of feed, each sow typically consuming 6 lbs of feed per day.

PEDV broke throughout the heard on day 1, which in captive herds typically cause 100% mortality in all piglets farrowed from infected sows for an average of four weeks.

On day 2, 440 weaned piglets 7 to 18 days old received a 2.2 g direct bolus dose of Ralco commercial product PacifiED, which comprises 48.7 wt. % commercial product Larafeed solids (Larch tree arabinogalactan), 17 wt. % Egg antibody, 13.2 wt. % RO water, 10 wt. % olive oil, 7.5 wt. % KCl powder, 2 wt. % potassium sorbate (45%), 1.1 wt. % sweeteners, and 0.3 wt. % EO oil, wherein the EO fraction comprises 80% oregano EO and 20% thyme EO (60 wt. % carvacrol, 11 wt. % thymol, 10 wt. % para-cymene, 19.0 wt. % other secondary thyme oil constituents). The same piglets received a 2.2 g direct bolus dose of Ralco commercial product First Pulse D, which comprises 49 wt. % commercial product Larafeed solids (Larch tree arabinogalactan), 35 wt. % colostrum extract, 10 wt. % olive oil, 2.85 wt. % RO water, 2 wt. % potassium sorbate (45%), 0.3 wt. % EOs, 0.5% sweeteners and 0.35 wt. % TIC gum. powder (Larch tree arabinogalactan) extract, 0.60 wt. % TIC gum, and 18.75 wt. % EOs. The EOs fraction comprised 60.4 wt. % carvacrol, 10.8 wt. % thymol, 9.9 wt. % paracymene, and 18.9% secondary oil constituents from oregano oil and thyme oil. The same piglets were given ~8.5 g of Ralco commercial product PreparED per day. PreparED comprises 53.75 wt. % RO Water, 22.5 wt. % commercial product Larafeed solids (Larch tree arabinogalactan), 11 wt. % Egg AB for 2052 PEDV/Rota, 5 wt. % Potassium Cl powder (1120 soluble), 3 wt. % Elyte Concentrate Premix, 2 wt. % Potassium Sorbate (45%), 1.5 wt. % Citric Acid, 0.75 wt. % flavoring, and 0.5 wt. % TIC Gum. At day 18, 60 piglets were dead with a 13.6% mortality.

On day 3, 421 piglets 2-8 days old were weaned into clean farrowing pens. All got 2.2 g of PacifiED and 2.2 g of First Pulse D and ~8.5 g per day of PreparED in milk. This litter had a 50% mortality rate. All piglets born on days 3 through day 7 died.

On day 8, Regano EX in feed was increased to 1.25 lbs per ton of feed through day 29, with each sow typically consuming 6 lbs of feed per day. Ralco commercial product RALCO SELECT, was mixed with sow drinking fluids in a ratio of 1:20 through day 13, with each sow typically drinking 12 gallons of fluids per day. RALCO SELECT comprising 67.9 wt. % RO water, 12.75 wt. % commercial product Larafeed powder (Larch tree arabinogalactan) extract, 0.60 wt. % TIC gum, and 18.75 wt. % EOs. The EOs fraction comprised 66.66% thyme oil (0.13% wt. % carvacrol, 30.5 wt. % thymol, 18.0 wt. % para-cymene, 18.0 wt. % other secondary thyme oil constituents) and 33.33% synthetic cinnamaldehyde. Piglets born on days 8 through 11 had a 90% mortality rate. Piglets born on day 12 received a 2.2 g direct bolus dose of PacifiED and a 2.2 g direct bolus dose of First Pulse D on day 12, and a 1.1 g direct bolus dose of PacifiED and a 1.1 g direct bolus dose of First Pulse D on days 13 and 14. This litter had a 46% mortality rate. On day 14 a piglet litter farrowed and had a 0% mortality rate.

The Antiviral efficacy of an EO composition against porcine epidemic diarrhea virus (PEDV) was also field-tested on a 3,000 sow farm. Ralco commercial product REGANO EX, had been regularly fed to the sows at 0.75 lbs of REGANO EX per ton of feed, with each sow typically consuming 6 lbs of feed per day, for nine months prior to the PEDV outbreak on day 1. Upon outbreak REGANO EX was increased to 1.25 lbs per ton of feed. All sows with piglets due within 5 days or less were given 2.5 g of REGANO 4XL for 5 days. All small piglets received 2.2 g of First Pulse D upon birth. Mortality rates for piglets was 90% on days 1-3, 80% to 90% on days 4-7, 50% on days 8-11, 40% to 30% on days 12-14, and less than 10% after day 14. On each farm, PEDV outbreaks were resolved in half the time of a typical outbreak duration.

Example 6

Anti-viral Efficacy of EO Composition Against Transmissible Gastroenteritis Virus (Obtained from the University of Minnesota)

In this trial, the antiviral effectiveness of REGANO 4XL against TGEV was determined. The REGANO 4XL was diluted with water and mixed at a 9:1 ratio with the viral inoculum to achieve a test system having an EO fraction of 50 ppm. Permissive host cell line used was porcine fetal testes. Contact time was 30 minutes at 20.0° C. with an organic soil load of 1% 1-13S. No appreciable cytotoxicity was observed. Results are given in Table 10.

TABLE 10

Antiviral Effects of EO Composition Against TGEV

| Dilution | Virus Control | Regano 4XL 50 ppm | Cytotoxicity Control Regano 4XL 50 ppm | Neutralization Control Regano 4XL 50 ppm |
|---|---|---|---|---|
| $TCID_{50}$/ 100 μL | $10^{4.50}$ | $10^{4.00}$ | $\leq 10^{1.50}$ | Neutralized at $\leq 1.50$ $\log_{10}$ |
| Percent Reduction | NA | 68.4% | NA | NA |
| Log Reduction | NA | 0.50 $\log_{10}$ | NA | NA |

Example 7

Anti-viral Efficacy of EO Compositions Against Enterovirus 71 (Strain ATCC VR-1432)

In this trial, the antiviral effectiveness of REGANO 4XL and RALCO SELECT against enterovirus 71 (Hand, Foot, and Mouth Disease) were determined. The REGANO 4XL was diluted with water and mixed at a 9:1 ratio with the viral inoculum to achieve a test system having an EO fraction of 50 ppm. The target viral inoculum was 6.00 $\log_{10}$ upon combination with the REGANO 4XL. Permissive host cell line used in all trials was Vero (ATCC CCL-81). Contact time included 10 and 30 minutes at 21.6° C. with an organic soil load of 5% heat activated HI-FBS. The results for REGANO 4XL are given in Table 11 below:

TABLE 11

Antiviral Effects of EO Composition Against Enterovirus 71

|  | Contact Times | Suspension Type | $Log_{10}$ per 0.1 ml | Mean $Log_{10}$ per Suspension | % Reduction vs Time Zero | $Log_{10}$ Reduction vs Time Zero |
|---|---|---|---|---|---|---|
| Enterovirus 71 (Hand, Foot and Mouth Disease Virus) | Time Zero | Control | 5.00<br>5.00 | 5.00 | N/A | N/A |
|  | 10 Minutes | Test | 5.00<br>5.00 | 5.00 | 0.00% | 0.00 |
|  | 30 minutes | Test | 4.75<br>4.50 | 4.63 | 57.83% | 0.38 |

The RALCO SELECT was diluted with water at various levels and mixed at a 9:1 ratio with the viral inoculum to achieve test systems having EO fractions of 250 ppm, 500 ppm, 750 ppm, and 1000 ppm. The target viral inoculum was 6.00 $Log^{10}$ per 0.1 mL upon combination with the REGANO 4XL. Contact time included 240, 180, 120, and 60 minutes, respectively, at ambient temperatures with no organic soil load. The results are given in Table 12 below.

TABLE 12

Antiviral Effects of EO Composition Against Enterovirus 71

|  | Contact Time | Test Substance | Log10 Infectious Units per 0.1 ml | Percent Reduction vs Control at Time Zero | Log10 Reduction vs Control at Time Zero | Percent Reduction vs Timed Control | Log10 Reduction vs Timed Control |
|---|---|---|---|---|---|---|---|
| Enterovirus 71 (ATCC VR-1432) | Time Zero | Control | 5.50 | N/A |  | N/A |  |
|  | 60 Minutes | Control | 5.50 |  |  |  |  |
|  |  | 1000 ppm | 5.00 | 68.38% | 0.50 | 68.38% | 0.50 |
|  | 120 Minutes | Control | 4.50 |  | N/A |  |  |
|  |  | 750 ppm | 4.75 | 82.22% | 0.75 | No Reduction |  |
|  | 180 Minutes | Control | 4.75 |  | N/A |  |  |
|  |  | 500 ppm | 4.50 | 90.00% | 1.00 | 43.77% | 0.25 |
|  | 240 Minutes | Control | 4.75 |  | N/A |  |  |
|  |  | 250 ppm | 4.75 | 82.22% | 0.75 | No Reduction |  |

Example 8

Anti-viral Efficacy of EO Composition Against Equine Herpesvirus-1 (Strain ATCC VR-2248)

In this trial, the antiviral effectiveness of RALCO SELECT against EHV-1 was determined. The RALCO SELECT was diluted with water and mixed at a 9:1 ratio with the viral inoculum to achieve a test system having an EO fraction of 50 ppm. The target viral inoculum was 6.00 $Log_{10}$ upon combination with the RERALCO SELECT. Permissive host cell line used Vero ATCC CCL-81. Contact times included 30 minutes, 60 minutes, 120 minutes, and 4 hours with an organic soil load was 5% LBS. No appreciable cytotoxicity was observed. The results are shown in Table 13:

TABLE 13

Antiviral Effects of EO Compositions Against Equine Herpesvirus-1

|  | Contact Times | Suspension Type | $Log_{10}$ per 0.1 ml | % Reduction vs Time Zero | $Log_{10}$ Reduction vs Time Zero | % Reduction vs Timed Control | $Log_{10}$ Reduction vs Timed Control |
|---|---|---|---|---|---|---|---|
| Equine Herpesvirus-1 | Time Zero | Control | 6.00 | N/A | N/A | N/A | N/A |
|  | 30 Minutes |  | 5.50 | 68.4% | 0.50 |  |  |
|  | 60 Minutes |  | 5.50 | 68.4% | 0.50 |  |  |
|  | 120 Minutes |  | 5.50 | 68.4% | 0.50 |  |  |
|  | 4 Hours |  | 5.50 | 68.4% | 0.50 |  |  |
|  | 30 Minutes | Test | 5.25 | 82.2% | 0.75 | 43.7% | 0.25 |
|  | 60 Minutes |  | 5.25 | 82.2% | 0.75 | 43.7% | 0.25 |
|  | 120 Minutes |  | 5.25 | 82.2% | 0.75 | 43.7% | 0.25 |
|  | 4 Hours |  | 4.75 | 94.4% | 1.25 | 82.2% | 0.75 |

Example 9

Anti-viral Efficacy of EO Composition Against Bovine Viral Diarrhea Virus (Strain ATCC VR-1422)

In this trial, the antiviral effectiveness of RALCO SELECT against BVDV was determined. The RALCO SELECT was diluted with water and mixed at a 9:1 ratio with the viral inoculum to achieve a test system having an EO fraction of 50 ppm. The target viral inoculum was 6.00 $Log_{10}$ upon combination with the RALCO SELECT. Permissive host cell line used was adult steer kidney cells ATCC CCL-22. Contact times included 30 minutes, 60 minutes, 120 minutes, and 4 hours with an organic soil load of 5% LBS. No appreciable cytotoxicity was observed. The results are given in Table 14 below:

TABLE 14

Antiviral Effects of EO Compositions Against Bovine Viral Diarrhea Virus

| | Contact Time | Test Substance | $Log_{10}$ Infectious Units per 0.1 ml | Percent reduction vs control at time zero | $Log_{10}$ reduction vs control at time zero |
|---|---|---|---|---|---|
| Bovine Viral Diarrhea Virus (VR-1422) | Time Zero | Control | 5.00 | N/A | |
| | 30 Minutes | 50 ppm | 5.25 | No Reduction | |
| | 60 Minutes | 50 ppm | 4.75 | 43.77% | 0.25 |
| | 2 Hours | 50 ppm | 4.50 | 68.38% | 0.50 |
| | 4 Hours | Control | 4.75 | 43.77% | 0.25 |
| | | 50 ppm | 4.00 | 90.00% | 1.00 |

Example 10: Anti-viral Efficacy of EO Composition Against Canine Parvovirus (Strain ATCC VR-2016)

In this trial, the antiviral effectiveness of REGANO 4XL against canine parvovirus was determined. The REGANO 4XL was diluted with water at various levels and mixed at a 9:1 ratio with the viral inoculum to achieve test systems having EO fractions of 250 ppm, 500 ppm, 1000 ppm, and 2000 ppm. The $TCID_{50}$ viral inoculum target was 6.00 log 10 per 0.41 upon combination with the REGANO 4XL. Permissive host cell line used was A-72 (dog tumor cells), ATCC CRL-1542. Contact time between the viral inoculum and the EO compositions was 4 hours, 3 hours, 2 hours and 1 hour for the 250 ppm, 500 ppm, 1000 ppm, and 2000 ppm trials, respectively, at 36° C. with no organic soil load. No appreciable cytotoxicity was observed. Results are given in Table 15.

TABLE 15

Antiviral Effects of EO Composition Against Canine Parvovirus

| | Contact Time | Test Substance | $Log_{10}$ Infectious Units per 0.1 ml | Percent Reduction vs Control at time Zero | $Log_{10}$ Reduction vs Control at Time Zero |
|---|---|---|---|---|---|
| Canine Parvovirus (ATCC VR-2016) | Time Zero | Control | 6.00 | N/A | |
| | 1 Hour | 2000 ppm | ≥5.50 | ≤68.38% | ≥0.50 |
| | 2 Hours | 1000 ppm | 5.00 | 90.00% | 1.00 |
| | 3 Hours | 500 ppm | ≥5.50 | ≤68.38% | ≥0.50 |
| | 4 Hours | Control | 5.50 | N/A | |
| | | 250 ppm | 5.00 | 90.00% | 1.00 |

Example 11

Anti-viral Efficacy of EO Composition Against Newcastle Disease (ATCC VR-108 Strain B1, Hitchner or Blacksburg)

In this trial, the antiviral effectiveness of RALCO SELECT against Newcastle disease was determined. The RALCO SELECT was diluted with water at various levels and mixed at a 9:1 ratio with the viral inoculum to achieve test systems having EO fractions of 125 ppm, 250 ppm, 500 ppm, and 1000 ppm. Permissive host cell line used was chicken embryo fibroblasts. Contact time between the viral inoculum and the EO compositions was 4 hours, 3 hours, 2 hours and 1 hour for the 125 ppm, 250 ppm, 500 ppm, and 1000 ppm trials, respectively, at 20.5° C. with no organic soil load. No appreciable cytotoxicity was observed. Results are given in Table 16.

TABLE 16

Antiviral Effects of EO Composition Against Newcastle Disease:

| | 125 ppm 4 Hours | 250 ppm 3 Hours | 500 ppm 2 Hours | 1000 ppm 1 Hour |
|---|---|---|---|---|
| TCID50/ 100 μL | $10^{4.75}$ | $10^{5.50}$ | $10^{5.75}$ | $10^{5.25}$ |
| Percent Reduction | 94.4% | 82.2% | No Reduction | 82.2% |
| Log Reduction | 1.25 $Log_{10}$ | 0.75 $Log_{10}$ | No Reduction | 0.75 $Log_{10}$ |

Example 12

Anti-viral Efficacy of EO Composition Against HIV-1 (Strain HTLV $III_B$)

In this trial, the antiviral effectiveness of REGANO 4XL against HIV-1 was determined. The REGANO 4XL was diluted with water at various levels and mixed at a 9:1 ratio with the viral inoculum to achieve test systems having EO fractions of 250 ppm, 500 ppm, 1000 ppm, and 2000 ppm. Permissive host cell line used was MT-2 (human CD4+ lymphocytes). Contact time between the viral inoculum and the EO compositions was 4 hours, 3 hours, 2 hours and 1 hour 250 ppm, 500 ppm, 1000 ppm, and 2000 ppm trials, respectively, at 21.0° C. with a 1% fetal bovine serum organic soil load. No appreciable cytotoxicity was observed. Results are given in Table 17.

TABLE 17

Antiviral Effects of EO Composition Against HIV-1

| | 1 hour 2000 ppm | 2 hours 1000 ppm | 3 hours 500 ppm | 4 hours 250 ppm |
|---|---|---|---|---|
| $TCID_{50}$/200 μL | ≤$10^{1.50}$ | ≤$10^{1.50}$ | ≤$10^{1.50}$ | ≤$10^{1.50}$ |
| Percent Reduction | ≥99.998% | ≥99.999% | ≥99.997% | ≥99.99% |

Example 13

Anti-viral Efficacy of EO Composition Against Bovine Rotavirus (ATCC VR-1290)

In this trial, the antiviral effectiveness of REGANO 4XL against Bovine Rotavirus was determined. The test system was created by mixing REGANO 4XL (250 ppm, 500 ppm, 750 ppm, and 1000 ppm) at a 9:1 ratio with the viral inoculum. Permissive host cell line used was MA-104 Clone 1 (Embryonic African Green Monkey Kidney Cells). Contact between the viral inoculum and the REGANO 4XL occurred at 37±2° C. for various durations with no organic soil load. No appreciable cytotoxicity was observed. Results are given in Table 18.

TABLE 18

Antiviral Effects of EO Composition Against Bovine Rotavirus:

| | Contact Time | Test Substance | $Log_{10}$ Infectious Units per 0.1 ml | Percent reduction vs control at time zero | $Log_{10}$ reduction vs control at time Zero |
|---|---|---|---|---|---|
| Bovine Rotavirus ATCC VR-1290 | Time Zero | Control | 5.50 | N/A | |
| | 1 Hour | Control | 5.75 | No Reduction Observed | |
| | | 1000 ppm | 4.50 | 90.00% | 1.00 |
| | 2 Hours | Control | 5.00 | 68.38% | 0.50 |
| | | 750 ppm | 3.75 | 98.22% | 1.75 |
| | 3 Hours | Control | 4.75 | 82.22% | 0.75 |
| | | 500 ppm | 4.00 | 96.84% | 1.50 |
| | 4 Hours | Control | 4.50 | 90.00% | 1.00 |
| | | 250 ppm | 3.50 | 99.00% | 2.00 |

Example 14

Anti-viral Efficacy of EO Composition Against Avian Influenza (H5N1) Virus

In this trial, the antiviral effectiveness of REGANO 4XL against Avian Influenza (H5N1) was determined. The test system was created by mixing REGANO 4XL (125 ppm, 250 ppm, 500 ppm, and 1000 ppm) at a 9:1 ratio with the viral inoculum. Permissive host cell line used was MDCK (canine kidney cells). Contact between the viral inoculum and the REGANO 4XL occurred at 21.0° C. for various durations with no organic soil load. No appreciable cytotoxicity was observed. Results are given in Table 9.

TABLE 19

Antiviral Effects of EO Composition Against Avian Influenza (H5N1):

| | 1000 ppm 30 Minute | 500 ppm 1 Hour | 250 ppm 2 Hour | 125 ppm 4 Hour |
|---|---|---|---|---|
| TCID50/ 100 μL | $10^{3.00}$ | $10^{5.50}$ | $10^{6.00}$ | $10^{5.50}$ |
| Percent Reduction | 99.97% | 90.0% | 43.8% | 82.2% |
| Log Reduction | 3.50 $Log_{10}$ | 1.00 $Log_{10}$ | 0.25 $Log_{10}$ | 0.75 $Log_{10}$ |

Example 15

Anti-viral Efficacy of EO Composition Against Duck Hepatitis B Virus (Accuratus Lab Services Strain 10/29/11)

In this trial, the antiviral effectiveness of REGANO 4XL against duck hepatitis B virus was determined. The test system was created by mixing REGANO 4XL (1000 ppm) at a 9:1 ratio with the viral inoculum. Permissive host cell line used was primary duck hepatocytes. Contact time between the viral inoculum and the EO compositions was 2 hours, at 20.5° C. with no organic soil load. A 94.4% reduction in viral titer was observed (a 1.25 $Log_{10}$ reduction), with no appreciable observed cytotoxicity.

Example 16

ORAC Capabilities of EO Compositions

ORAC capabilities of EO compositions were tested Brunswick Labs, Massachusetts. Table 20 illustrates the antioxidant ability of several embodiments provided herein, as compared to an industry standard antioxidant, Vitamin E. Results are expressed as trolox equivalents (TE/100 g) for each composition:

TABLE 20

ORAC (TE/100 g)Capabilities of Antiviral EO Compositions

| Oxygen species | Synergy Essence | Natural Vitamin E | Arabinogalactan |
|---|---|---|---|
| Peroxyl radical | 430400 | 2100 | 20600 |
| Hydroxyl radical | 1580000 | 0 | 46400 |
| Peroxynitrite | 6100 | 0 | 1200 |
| Superoxide anion | 0 | 0 | 16600 |
| Singlet oxygen | 284100 | 37100 | 11600 |
| Total ORAC | 2300600 | 39200 | 96400 |

What is claimed is:

1. A method of inhibiting a virus within a subject or system, the method comprising:
    administering a treatment composition combined with a carrier to one or more of a subject and system, wherein the treatment composition is an emulsion consisting of:
    thyme essential oil and oregano essential oil, wherein one or more of the thyme essential oil and oregano essential oil provides effective amounts of carvacrol, thymol, and p-cymene,
    an emulsifier selected from a tannin compound, larch arabinogalactan, and combinations thereof, and
    water,
    wherein the essential oils are present as an emulsion and the average particle size of the essential oils in the emulsion is 25 microns or less.

2. The method of claim 1, wherein the virus comprises any virus included in Baltimore Classification groups I through VII.

3. The method of 1, wherein the subject comprises one or more of humans, swine, bovine, horses, fowl, shrimp, fish, and deer.

4. The method of claim 1, wherein inhibiting a virus comprises preventing or slowing a proliferation of the virus in the subject or system, or reducing a viral presence within the subject or system.

5. The method of claim 1, wherein the virus comprises human immunodeficiency virus.

6. The method of claim 1, wherein the tannin compound is tannic acid.

7. The method of claim 1, wherein the treatment composition is present as an emulsion without use of an organic solvent.

8. The method of claim 1, wherein the treatment composition is about 50% thyme essential oil and about 50% oregano essential oil.

9. The method of claim 1, wherein the treatment composition is about 20% thyme essential oil and about 80% oregano essential oil.

10. The method of claim 1, wherein the effective amounts of carvacrol, thymol, and p-cymene are at least about 55% carvacrol, about 5%-15% thymol, and about 5%-15% p-cymene.

11. The method of claim 1, wherein the carrier is animal feed.

12. A method of inhibiting a virus within a subject or system, the method comprising:
administering a treatment composition combined with a carrier to a subject or system,
wherein the treatment composition is an emulsion consisting of:
thyme essential oil and synthetic cinnamaldehyde, wherein one or more of the thyme essential oil and synthetic cinnamaldehyde provides effective amounts of carvacrol, thymol, and p-cymene; and
an emulsifier selected from a tannin compound, larch arabinogalactan, and combinations thereof; and
water;
wherein the essential oils are present as an emulsion and the average particle size of the essential oils in the emulsion is 25 microns or less.

13. The method of claim 12, wherein the treatment composition is about 66.7% thyme and about 33.3% synthetic cinnamaldehyde.

14. The method of claim 12, wherein the effective amounts of carvacrol, thymol, and p-cymene are less than about 1% carvacrol, about 25%-35% thymol, and about 15%-35% p-cymene.

15. The method of claim 12, wherein the thyme essential oil is oil derived from plants in the *Thymus* genus.

* * * * *